United States Patent [19]
Heinonen et al.

[11] Patent Number: 5,904,188
[45] Date of Patent: May 18, 1999

[54] ARRANGEMENT FOR PREVENTING OVERFILL OF AN ANAESTHETIC LIQUID CONTAINER

[75] Inventors: Erkki Heinonen; Jukka Kankkunen, both of Helsinki, Finland

[73] Assignee: Instrumentarium Oy, Helsinki, Finland

[21] Appl. No.: 09/066,060

[22] Filed: Apr. 24, 1998

Related U.S. Application Data

[63] Continuation-in-part of application No. 08/769,957, Dec. 19, 1996, abandoned.

[30] Foreign Application Priority Data

Dec. 29, 1995 [FI] Finland ..................................... 956354
Apr. 18, 1996 [FI] Finland ..................................... 961698

[51] Int. Cl.$^6$ .................................................. A61M 16/00
[52] U.S. Cl. ........................... 141/18; 141/236; 141/285; 141/308; 141/392
[58] Field of Search .............................. 141/18, 236, 285, 141/308, 392; 128/200, 24, 203.12

[56] References Cited

U.S. PATENT DOCUMENTS

| | | | |
|---|---|---|---|
| 3,536,108 | 10/1970 | Schreiber | 141/18 |
| 3,565,133 | 2/1971 | Jones | 141/308 |
| 3,578,042 | 5/1971 | Breiling | 141/301 |
| 4,715,370 | 12/1987 | Altner et al. | 128/203.12 |
| 5,398,737 | 3/1995 | Heinonen et al. | 141/285 |
| 5,474,112 | 12/1995 | Carola | 141/7 |
| 5,478,506 | 12/1995 | Lavimodiere | 261/72.1 |
| 5,611,375 | 3/1997 | Kankkunen et al. | 141/18 |
| 5,617,906 | 4/1997 | Braatz et al. | 141/21 |

FOREIGN PATENT DOCUMENTS

| | | |
|---|---|---|
| 664138 | 7/1995 | European Pat. Off. . |
| 35 44 392 | 5/1987 | Germany . |
| 2279016 | 12/1994 | United Kingdom . |

*Primary Examiner*—J. Casimer Jacyna
*Attorney, Agent, or Firm*—Andrus, Sceales, Starke & Sawall

[57] ABSTRACT

An arrangement for preventing overfill of an anaesthetic liquid container of a vaporizer resulting from inclination, comprising a bent intermediate container for guiding anaesthetic liquid to the anaesthetic liquid container for vaporization and for removing a volume of gas equivalent to the filling of anaesthetic liquid from the anaesthetic liquid container. The intermediate container is arranged to form a common conduit for the anaesthetic liquid and the gas removed from the container, and to combine the liquid flow outlet level and the gas flow outlet level in such a way that the anaesthetic liquid is allowed to flow into the anaesthetic liquid container only when the liquid flow outlet level is below the gas flow outlet level. The bent intermediate container may be located interiorly of, or exterior to, the anaesthetic liquid container.

19 Claims, 8 Drawing Sheets

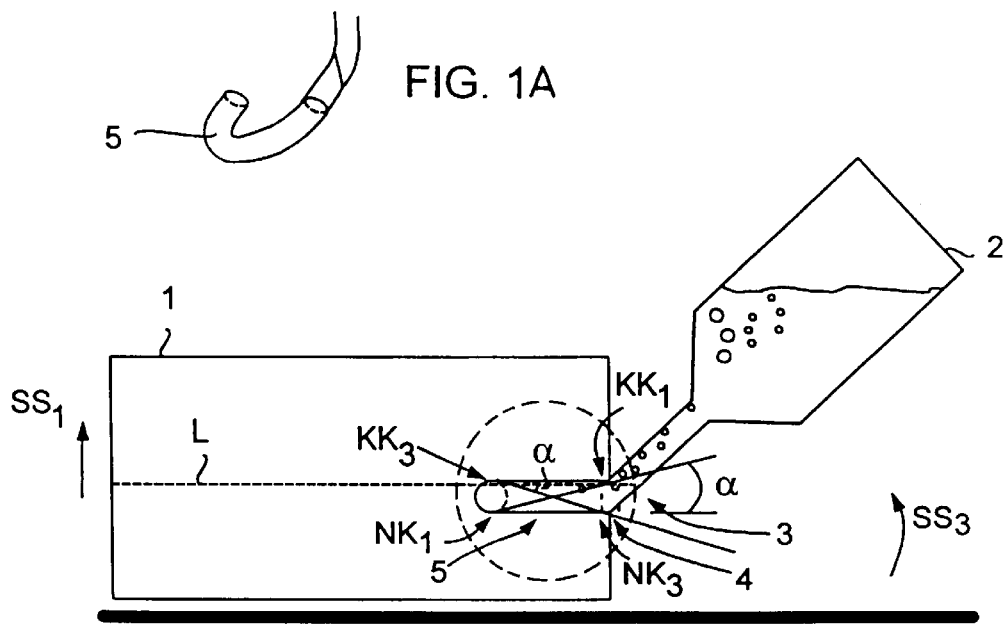
FIG. 1A
FIG. 1
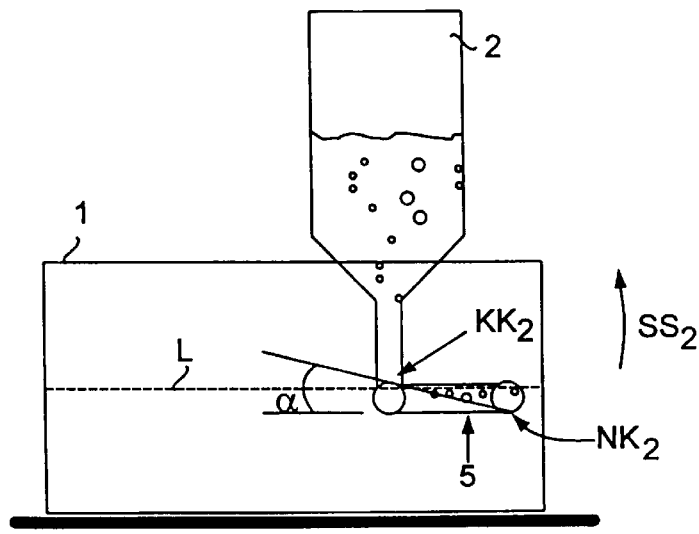
FIG. 2

FIG. 8A
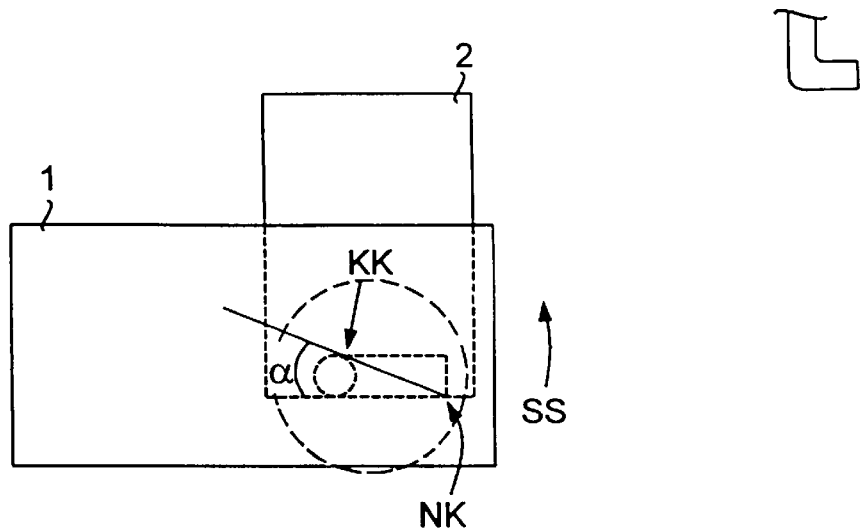
FIG. 8
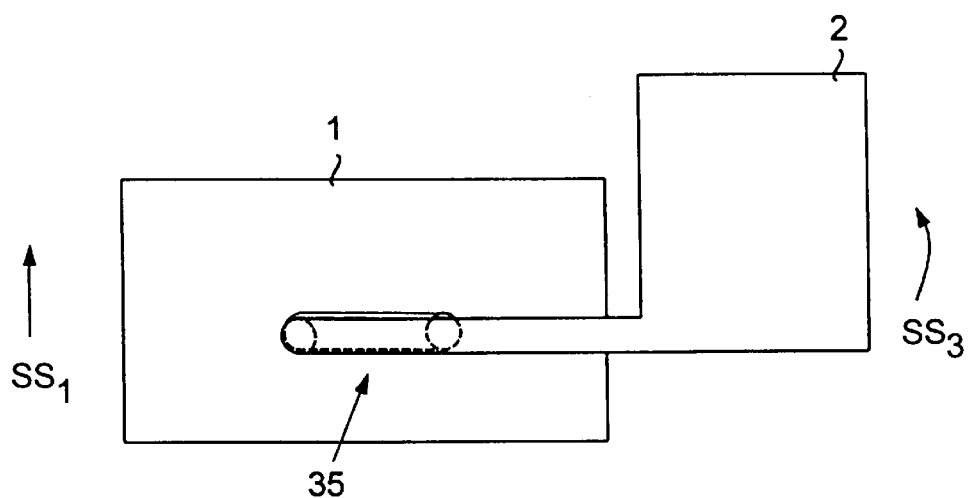
FIG. 9

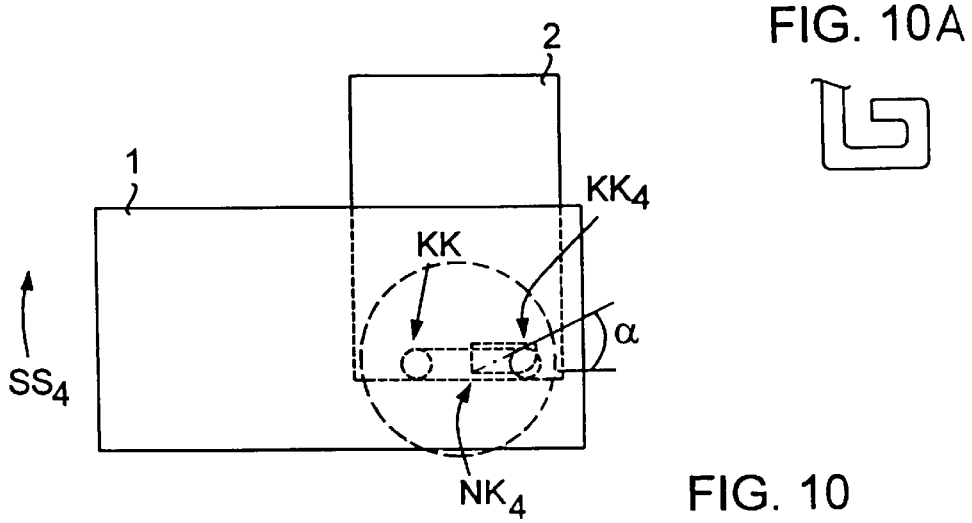
FIG. 10
FIG. 10A
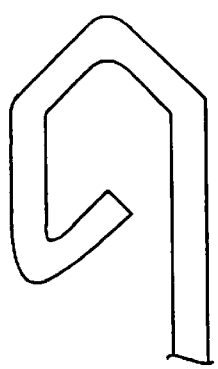
FIG. 11
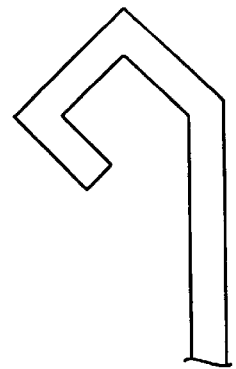
FIG. 12
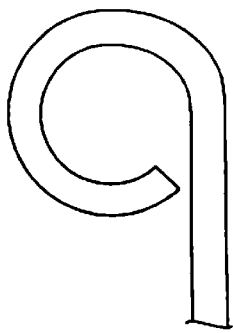
FIG. 13
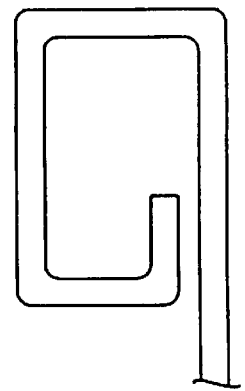
FIG. 14

ARRANGEMENT FOR PREVENTING OVERFILL OF AN ANAESTHETIC LIQUID CONTAINER

CROSS-REFERENCE TO RELATED APPLICATIONS

The present application is a continuation-in-part application of U.S. patent application Ser. No. 08/769,957, filed Dec. 19, 1996, now abandoned.

BACKGROUND OF THE INVENTION

The invention relates to an arrangement for preventing overfill of an anaesthetic liquid container, comprising means for guiding anaesthetic liquid to the anaesthetic liquid container for vaporization and for removing a volume of gas equivalent to the filling of anaesthetic liquid from the anaesthetic liquid container.

In order for anaesthetic vaporizers functioning on the bypass-saturation principle to operate correctly, the amount of liquid in the liquid container should not exceed an allowable level. If the level should be exceeded, the liquid might block the flow conduit which passes through the liquid container and carries the gas flow to be supplied to the patient. The gas flow can, however, pressurize the liquid container, forcing thus extra liquid out, which results in serious over-administration. For the above reasons, to limit the amount of liquid, vaporizers are provided with a device which prevents them from being filled over the maximum allowable amount of liquid.

The filling of the liquid container of an anaesthetic vaporizer is based on the exchange of volumes in the vaporizer and the supply container for liquid. When liquid flows into the vaporizer, an equivalent volume of gas flows out of it. Correspondingly, when liquid flows out of the supply container, an equivalent volume of gas flows into it. The filling of the vaporizer stops if either or both of the replacement gas flows is/are exhausted.

There are three different types of systems for filling vaporizers: funnel, filler and tube.

In a funnel-type system the anaesthetic liquid is poured from the supply container, i.e. a bottle, to the funnel openly through the external atmosphere. The filling of the container stops, when the liquid surface closes the opening of the funnel that faces the vaporizer, and the gas flow is prevented from flowing out of the vaporizer. Such a system is described, for example, in British Patent No. 1,224,478.

A filler-type system is used to connect the vaporizer and the bottle to each other. In this case, the filling system is closed, and anaesthetic liquid is not allowed to vaporize to the external atmosphere. The filler comprises two tubes: one carries liquid from the bottle to the vaporizer, and the other carries gas from the vaporizer to the bottle. The filler is also standardized, e.g. prEN 1280. The filling of the container stops when the vaporizer is filled to such an extent that the liquid surface reaches the gas conduit.

The tube-type system is also a closed system. In this system, the filling head of the bottle is placed in a filling device provided in the vaporizer. A tight conduit is thus formed between the bottle and the vaporizer, and the valves in both the bottle and the vaporizer are opened. Such a system is disclosed, for example, in PCT publications WO 92/12753 and WO 95/08361. The filling stops when the vaporizer is filled such that the liquid surface reaches the upper edge of the tube.

The solutions described above have the common feature that they are all positioned on a side of the vaporizer. The vaporizer can thus be overfilled if it is tilted in such a way that the edge facing the filling device rises relative to the liquid container. If the filling device falls below the liquid container as a result of tilting, the filling will stop too soon, which does not represent a safety risk in the operation of the device.

Finnish Patent No. 94097 provides a solution for the problem described above. According to this solution, the liquid conduit is provided with an inclined portion in which a ball is positioned. When the vaporizer is tilted such that the filling device rises above the liquid container, the inclination direction of the inclined conduit changes, and the ball in the conduit rolls to a sealing surface at the other end of the conduit, closing thus the liquid flow conduit. This solution is particularly suitable for filler-type devices, in which the liquid and gas flow in opposite directions in separate conduits. It is not suitable for arrangements in which the liquid and gas flow in the same conduit.

BRIEF SUMMARY OF THE INVENTION

The object of the present invention is to provide an arrangement by which the drawbacks of the prior art can be obviated. This is achieved with an arrangement of the invention, which is characterized in that an intermediate container which is formed from a curved tubular portion and which is substantially horizontal in relation to the normal operative position of the anaesthetic liquid container is provided in connection with the anaesthetic liquid container, said intermediate container being arranged to form a common conduit for the anaesthetic liquid and the gas removed from the anaesthetic liquid container, and said intermediate container being arranged to combine the liquid flow outlet level and the gas flow outlet level of the filling port and the anaesthetic liquid container in such a way that the anaesthetic liquid is allowed to flow into the anaesthetic liquid container only when the liquid flow outlet level is below the gas flow outlet level.

It is an advantage of the invention that it allows overfill to be prevented in all the above-mentioned different types of filling systems. In the case of a filler-type system, the vaporizer-emptying property is lost, but during the filling the invention works well even in this system. Another advantage of the invention is its simplicity, whereby the start-up and operating costs will be low. On account of the simplicity, the arrangement is also reliable.

Various other features, objects, and advantages of the invention will be made apparent from the following detailed description and the drawings.

BRIEF DESCRIPTION OF THE SEVERAL VIEWS OF THE DRAWING

In the following, the invention will be described in greater detail by means of the preferred embodiments illustrated in the accompanying drawings, in which FIG. 1 is a schematic side view of an arrangement of the invention during filling in normal position;

FIG. 1A is a detailed, schematic, perspective view of the portion of FIG. 1 encircled by the dashed line;

FIG. 2 is a view of the arrangement of FIG. 1 in the longitudinal direction of the container;

FIGS. 7 and 8 are schematic views of a second embodiment of the invention from different directions;

FIG. 8A is a top view of the element encircled by a dashed line in FIG. 8;

FIGS. 9 and 10 are schematic views of a third embodiment of the invention from different directions;

FIG. 10A is a top view of the element encircled by the dashed line in FIG. 10;

FIGS. 11 to 14 show examples of different possible shapes of an intermediate container;

DETAILED DESCRIPTION OF THE INVENTION

Figure 3:
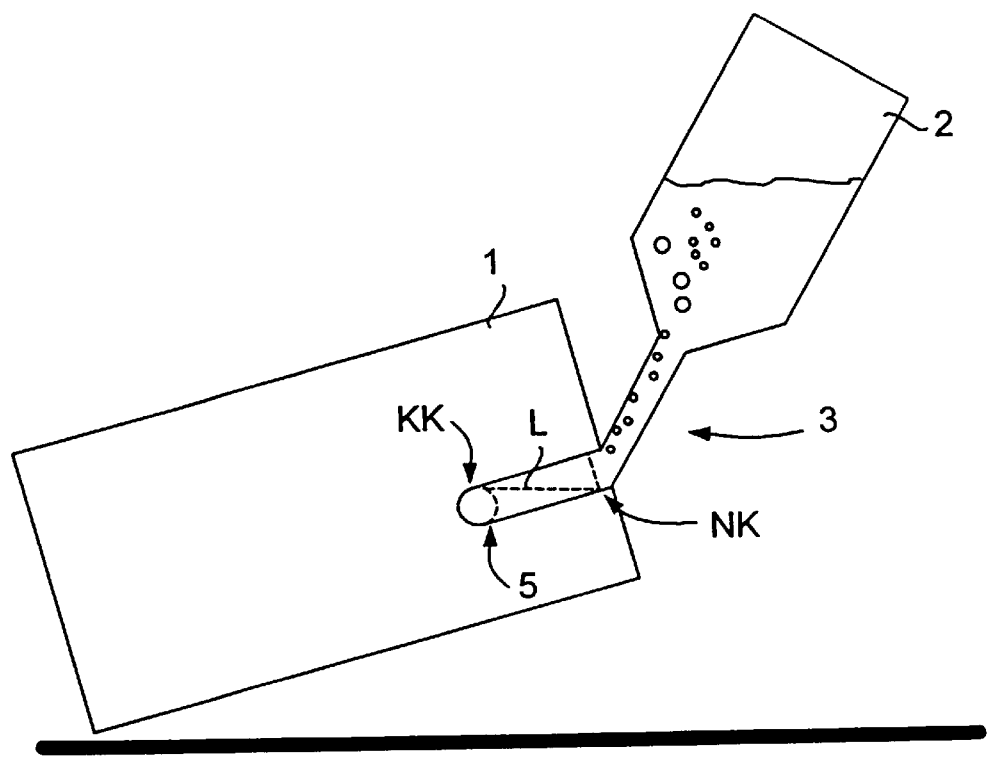
FIG. 3 is a schematic side view of the arrangement of FIG. 1 during filling in which the container is tilted along one edge.
Figure 4:
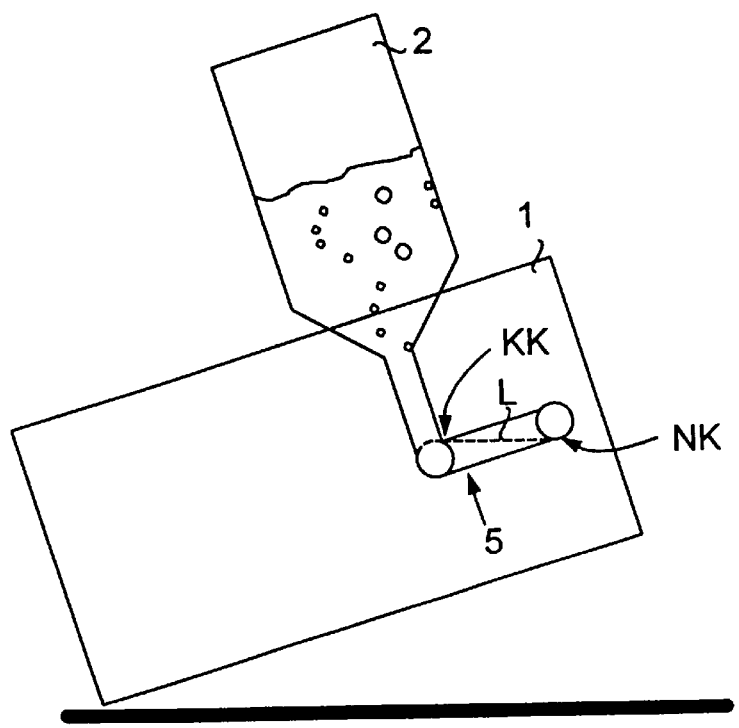
FIG. 4 is a view in the longitudinal direction of the container showing the container tilted during filling.

FIGS. 1 to 4 illustrate a preferred embodiment of the invention. Reference numeral 1 indicates an anaesthetic liquid container into which anaesthetic liquid is supplied for vaporization. The anaesthetic liquid is supplied into the anaesthetic liquid container from a supply container 2, such as a bottle. The arrangement further comprises means 3 for guiding the anaesthetic liquid into the anaesthetic liquid container 1 for vaporization and for removing an amount of gas equivalent to the filling of liquid from the anaesthetic liquid container 1 and for conducting the replacement gas into the supply container 2. The means 3 comprise, for example, a conduit through which the anaesthetic liquid and the volume of gas equivalent to the volume of liquid can flow into and out of the container, and necessary connector means for fixing the supply container 2 tightly to the filling port 4 of the anaesthetic liquid container.

The above-mentioned features represent fully conventional technology to one skilled in the art, wherefore they will not be described more closely herein. With respect to these features, reference is made, for example, to the above-mentioned publications representing the background art.

Figure 21:
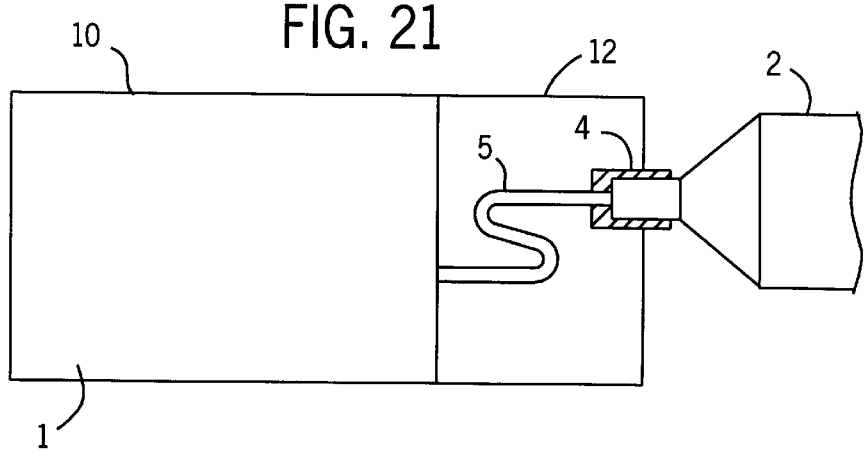
FIGS. 21 and 22 show further embodiments of the present invention with locations for the intermediate container differing from that shown in FIG. 1, et seq.
Figure 22:
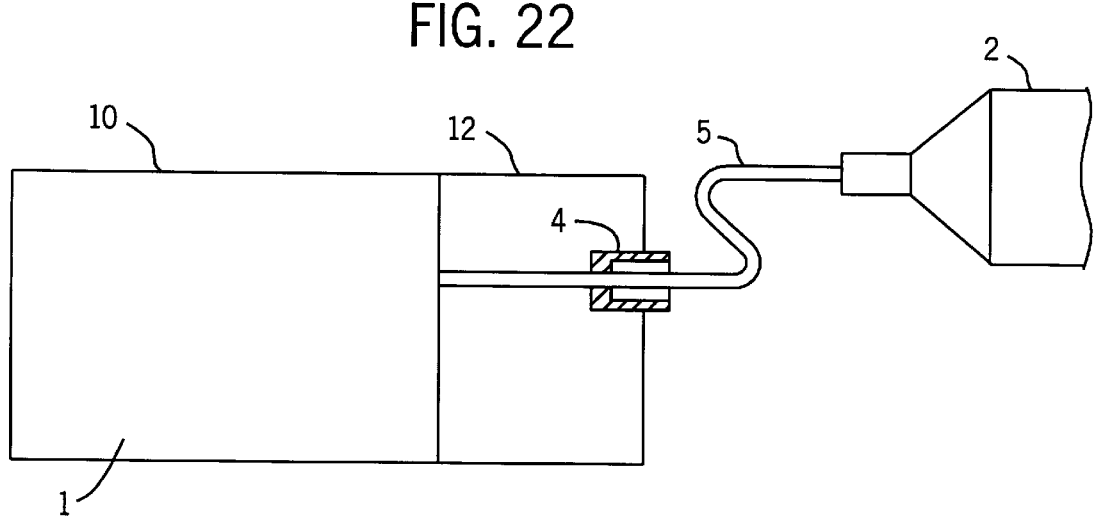

The essential feature of the invention is that the anaesthetic liquid container 1 is provided with an intermediate container 5 which is formed from a curved tubular member and which is substantially horizontal in relation to the normal operative position of the anaesthetic liquid container 1. The intermediate container 5 is arranged to provide a common conduit for the anaesthetic liquid and the gas removed from the anaesthetic liquid container 1. In the embodiment of FIGS. 1 to 4, the intermediate container is mounted between the filling port and the anaesthetic liquid container, i.e. inside the anaesthetic liquid container 1. However, this is not the only possibility, as the intermediate container may also belong, for example, to the supply container 2, as shown in FIG. 22. In the embodiment shown in FIG. 22, the intermediate container 5 can be integral with the supply container 2 or can comprise a separate element formed so that it can be coupled to the supply container 2 and the filling port 4 in the correct way. Or, the intermediate container may be located inside vaporizer 10 but outside the anaesthetic liquid container 1, as in the filling head 12, as shown in FIG. 21.

The intermediate container 5 is arranged to combine the outlet level for the liquid flow, i.e. the liquid threshold NK, and the outlet level of the gas flow, i.e. the gas threshold KK, in the filling port 4 and the anaesthetic liquid container 1 in such a way that the anaesthetic liquid is allowed to flow to the anaesthetic liquid container 1 only when the liquid flow outlet level NK is below the gas flow outlet level KK. In FIGS. 1 and 2, the subindexes 1 to 3 with the outlet levels NK and KK for the liquid and gas flows refer to the similarly indexed protection directions SS, i.e. the directions of the inclinations to be protected.

The solution is thus based on an intermediate container 5 formed from a curved tubular member. In the embodiment illustrated in FIGS. 1 to 4, the intermediate container 5 is positioned between the filling port 4 and the liquid container 1. The intermediate container 5 contains a common flow conduit for the liquid and gas flow. Thus the liquid flow outlet level NK and the gas flow outlet level KK are combined in a certain way, i.e. the liquid is allowed to flow from the bottle 2 to the liquid container 1 of the vaporizer only when the liquid flow outlet level NK is below the gas flow outlet level KK. Otherwise the intermediate container 5 is filled with liquid until the liquid surface reaches the gas flow outlet level KK, whereby the flow of replacement gas to the bottle 2 is cut off and the filling stops. The intermediate container 5 is mounted in the liquid container 1 in such a manner that the liquid flow outlet level, i.e. the liquid threshold NK, is below the gas flow outlet level, i.e. the gas threshold KK, in the allowable filling position, and rises above it if the vaporizer is turned to a position in which filling is not allowable.

In the example shown in FIGS. 1 to 4, the intermediate container 5 is made from a substantially U-shaped tube which is provided as an extension of the filling tube and which is preferably horizontal in relation to the normal operative position of the anaesthetic liquid container. The volume of the U-shaped tube serves as the intermediate container 5. The shape of the tube can be clearly seen from FIG. 1A, in which the circled portion of FIG. 1 is also shown as a schematic perspective view. The liquid flow outlet level, i.e. the liquid threshold NK, is the highest point of the bottom of the flow conduit formed by the intermediate container 5. The gas flow outlet level, i.e. the gas threshold KK, in turn, is the lowest point of the top of the above-mentioned flow conduit. In the U-shaped tube according to the example shown in the figure, the liquid threshold NK is formed at the opening of the tube facing the vaporizer, whereas the gas threshold is formed in the upper part of the tube, at the locations indicated in the figures. When the vaporizer is tilted in such a way that the filling device rises above the liquid container 1, the liquid threshold NK rises above the gas threshold KK, and the filling stops. When the liquid flows from the supply container 2 towards the vaporizer, a liquid seal will be formed in the bend of the U-shaped tube which forms the intermediate container 5. This liquid seal will prevent replacement gas from flowing to the supply container 2, whereby filling is prevented when the vaporizer is tilted. Such a situation is shown as a schematic view in FIGS. 3 and 4. The level of the liquid surface in which the filling stops is indicated in the figures by a broken line L. In addition, FIGS. 1 and 2 show the closing angle $\alpha$ whose significance is illustrated in principle in FIGS. 5 and 6.

Figure 5:
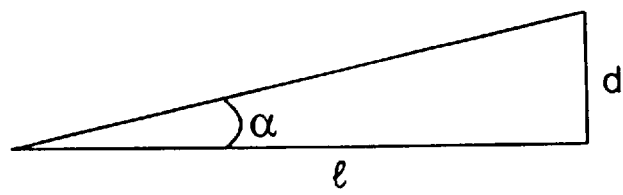
FIGS. 5 and 6 are schematic views of the correlations associated with the closing angle.

In FIG. 5, the term l represents the length of the straight portion of the tube. In the bend of the tube, length may herein also refer to the length of its projection. The term d represents the diameter of the tube.

It can be seen from FIG. 5, that $l = d \cot \alpha$. For example, if $d = 7$ mm and $\alpha = 10°$, then $l = 40$ mm. In reality, the closing angle will be smaller because of the surface tension and viscosity of the liquid. If filling is to be prevented even in the inverted position, the flow conduit must comprise a portion whose projection in vertical direction is greater than the diameter of the tube and which in the normal filling position extends downwards.

Figure 6:
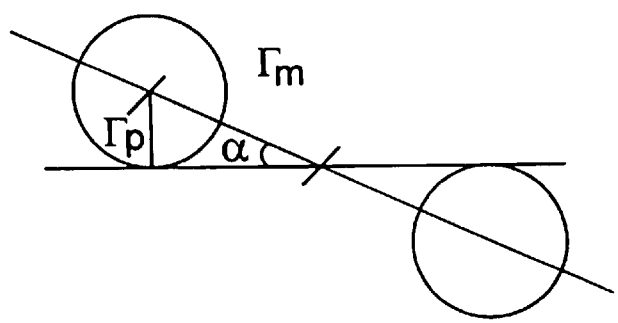

FIG. 6 illustrates the correlation between the diameter of the tube and the radius of curvature $r_m$ of the tube bend. It appears from FIG. 6 that the correlation between the tube diameter $r_p$ and the radius of a curvature $r_m$ of the tube bend is determined by the formula $\sin\alpha = r_p/r_m$.

Figure 7:
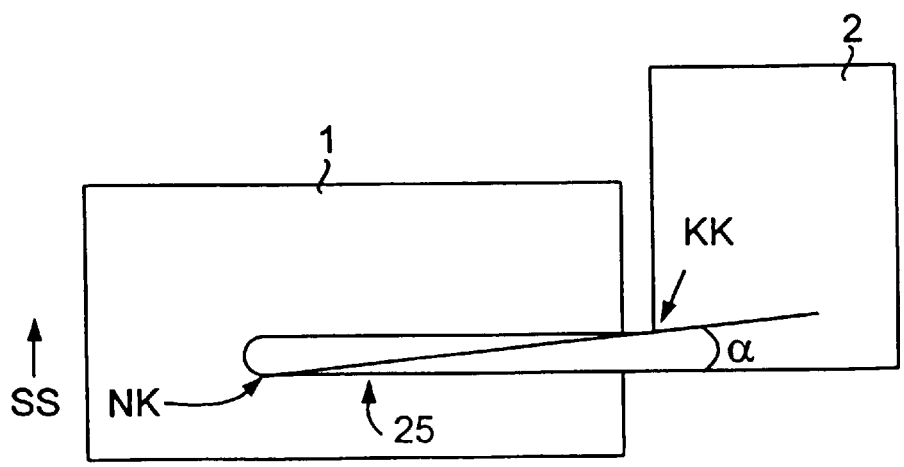

FIGS. 7 and 8 illustrate a second preferred embodiment of the arrangement of the invention. In this embodiment, the intermediate container 25 consists of a tubular portion which forms a bend of 90°, as shown in FIG. 8A, the bend being on a substantially horizontal plane in relation to the normal operative position of the anaesthetic liquid container. The liquid flow outlet level NK, the gas flow outlet level KK and the closing angle α are also indicated in FIGS. 7 and 8 in the same way as in FIGS. 1 to 6.

FIGS. 9 and 10 illustrate a third preferred embodiment of the arrangement of the invention. In this embodiment, the intermediate container 35 consists of a substantially horizontal tubular portion which forms a bend of 270° as shown in FIG. 10A. The shape of the tubular portion is shown in FIG. 10 in the same way as in FIGS. 7 and 8. Some of the liquid flow outlet levels NK, gas flow outlet levels KK and closing angles α are indicated in FIGS. 9 and 10 on the same grounds as in the preceding examples. In FIG. 10, subindex 4 refers to a corresponding protection direction $SS_4$. As regards protection directions $SS_1$ and $SS_3$, the outlet levels NK and KK and the closing angles α are the same as in the embodiment of FIGS. 1 and 2, where the tubular portion forms a bend of 180°. In the protection direction, the liquid would have to flow uphill and the gas downhill.

It should thus be noted that the intermediate container can be formed in many different ways. In its simplest, the tubular portion forming the intermediate container can be, for example, a tube as shown in FIGS. 1 and 7, which should however be carefully positioned. The curved tubular portion, in turn, may form a bend of e.g. 90°, 180°, 270°, 360° or even greater. As shown in FIGS. 21 and 22 the intermediate container may have an S-shape. The curved shape can be provided in different ways, even by means of a tube that turns stepwise. The term "curved" should be understood as a principle, the implementation of which may vary as shown below in FIGS. 11 to 14 and 15 to 22, for example. The tubular portion can be bent so as to form a spiral. If the bending angle is 270° or greater, a liquid seal is formed irrespective of the inclination angle and the position of the intermediate container. With smaller bending angles, a liquid seal is not formed in all inclination directions with the same inclination angles, but the intermediate container must then be placed in a correct position in the container to obtain a good result.

As stated above, the shape of the tubular portion forming the intermediate container may vary. FIGS. 11 to 14 show additional examples of various shapes of intermediate containers. The desired liquid level is determined by the positioning of the intermediate container in the vertical direction of the liquid container. When the container is filled above the liquid threshold, the liquid surface will form the liquid threshold. When the liquid surface rises to the level of the gas threshold, the filling stops. The stopping of the filling also depends on the viscosity and surface tension of the liquid.

Figure 15:
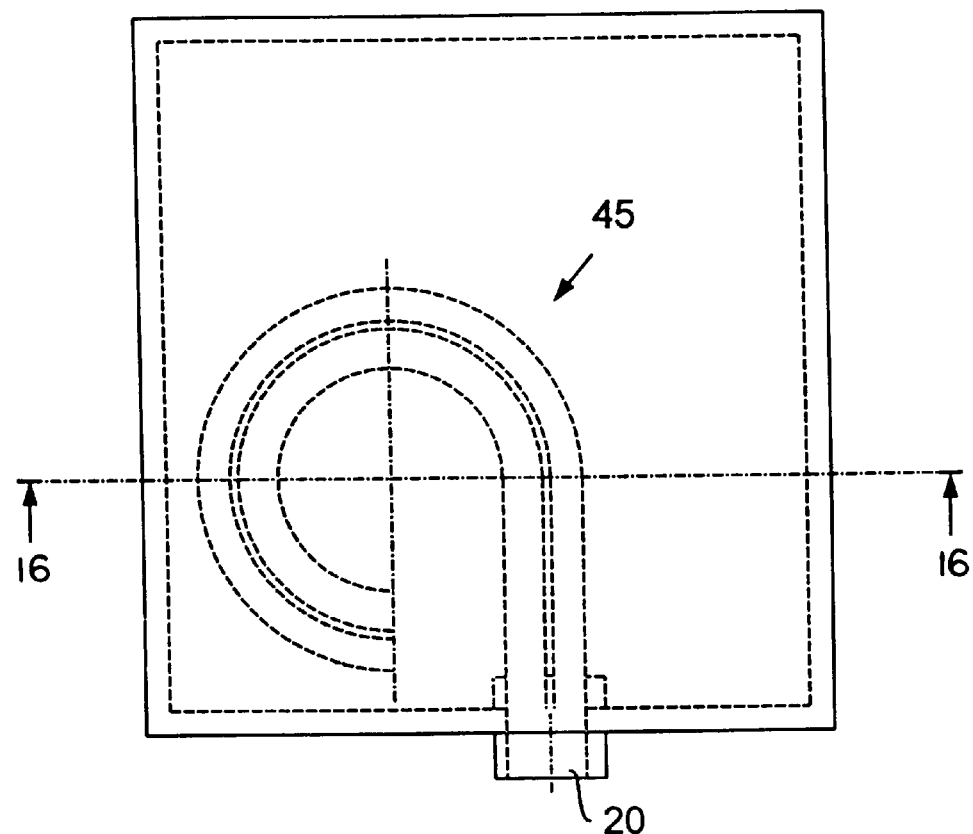
FIGS. 15 to 16 are schematic views of a fourth embodiment of the invention from different directions.
Figure 16:
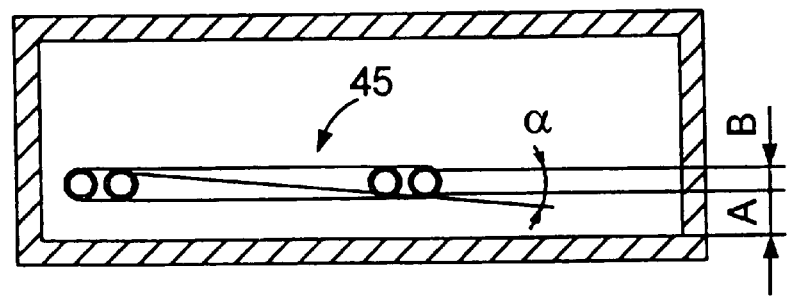

FIGS. 15 and 16 are schematic views of a fourth embodiment of the invention. FIGS. 17 to 20, in turn, illustrate variations of the embodiment of FIGS. 15 and 16.

In the embodiments described above, the intermediate containers are made from one tube. However, this is not the only possibility. In the embodiment of FIGS. 15 and 16, the intermediate container 45 is formed from two tubes which are substantially horizontal in relation to the normal operative position of the anaesthetic liquid container and which are mounted on the same plane, parallel to one another. The cross-section shape of the tubes can be selected fully freely: it may be circular, square, etc. The embodiment of FIGS. 15 and 16 has the advantage that the maximum surface level is can be accurately controlled, and the container is filled close to the maximum level at an even rate. In FIG. 16, letter A indicates the area in which filling takes place at a constant rate, and letter B the area in which filling takes place at a rate which decelerates according to the degree of fullness. It should be noted that a small inclination angle α is achieved with the solution. There may also be more than two parallel tubes. A construction with a plurality of tubes can be preferably implemented by means of a portion forming a common inlet space 20, as shown in FIG. 15.

Figure 17:
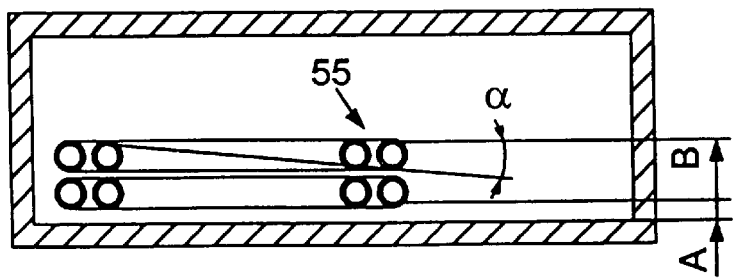
FIGS. 17 to 20 show different variations of the embodiment of FIGS. 15 and 16.
Figure 18:
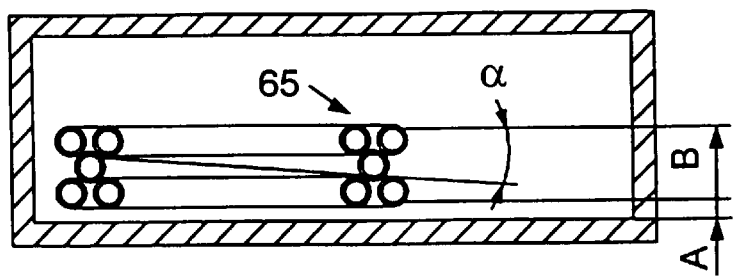

FIGS. 17 and 18 show different variations of the embodiment of FIGS. 15 and 16. In the solutions of FIGS. 17 and 18, the tubes that form the intermediate container 55, 65 are on different planes. In these solutions, too, the cross-section shapes of the tubes can be fully freely selected. The solutions of FIGS. 17 and 18 operate in the same way as the solution of FIGS. 15 and 16. The difference is that the area B of decelerating filling is larger than in the solution of FIGS. 15 and 16. When the liquid surface rises to the lowest tube, the liquid flow starts to slow down, and it stops when the liquid surface reaches the upper surface of the inner opening of the uppermost tube.

Figure 19:
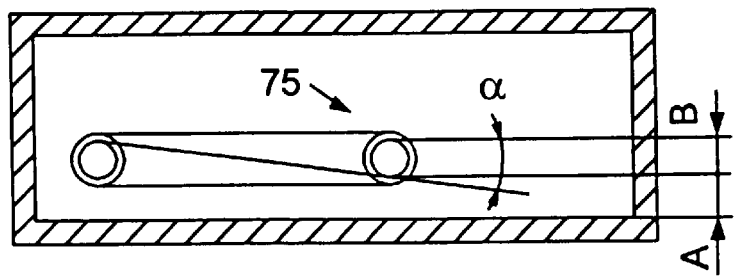

FIG. 19 shows a variation of the solutions of FIGS. 15–16 and 17–18. In this solution, the intermediate container 75 is made from one tube in such a way that the area of the tube is equal to the combined area of the tubes in the solution of FIG. 17, for example. A greater inclination angle is achieved with the solution of FIG. 19 than, for instance, with the solution of FIG. 17.

Figure 20:
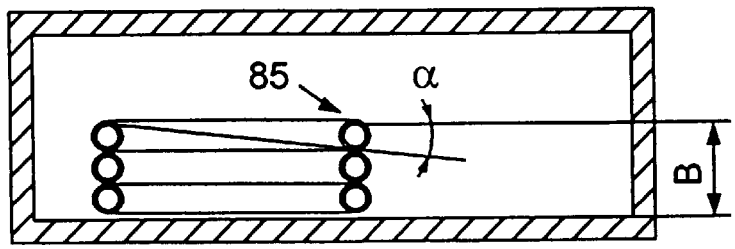

FIG. 20 illustrates a solution in which the tubes forming the intermediate container 85 are mounted on different planes on top of one another. In this solution, the filling rate decelerates as the degree of fullness grows, i.e. when one tube is blocked, the filling rate decelerates accordingly. In this solution, too, the cross-section shapes of the tubes can be selected freely. In the examples of the figures, the tubes are mounted in succession, parallelly and/or on top of one another. The tubes can be mounted on the same plane or on different planes, or both on the same and on different planes.

The examples described above are in no way intended to limit the invention, but the invention may be modified fully freely within the scope of the appended claims. It will therefore be clear that the arrangement of the invention or its details need not be precisely as shown in the figures, but other solutions are possible. According to the figures, the intermediate container is made from a tube with a circular cross-section. As has already been stated in connection with some examples, it is not necessary to use a tube with a circular cross-section, but the intermediate container may also be formed from a tube whose cross-section is square, oval, triangular, etc.

We claim:

1. An arrangement for filling an anaesthetic liquid container of a vaporizer with anaesthetic liquid to a desired level, said anaesthetic liquid being supplied from a supply container, said anaesthetic liquid container having a normal operative orientation with respect to a horizontal reference plane, said arrangement limiting the filling of the anaesthetic liquid container when the anaesthetic liquid container is tilted with respect to the horizontal reference plane, said arrangement comprising:

an intermediate container forming a flow path between said supply container and the interior of said anaesthetic liquid container for discharging anaesthetic liquid from the supply container into the anaesthetic liquid container and for removing a volume of gas from the anaesthetic liquid container to the supply container, said intermediate container comprising a tubular member having a pair of ends, one of which is open to the interior of the anaesthetic liquid container and the other of which receives anaesthetic liquid from said supply container, said tubular member being positioned to lie generally horizontally when said anaesthetic liquid container is in the normal operative orientation, said tubular member being bent intermediate its ends by a bend lying generally horizontally, at least a portion of said intermediate container forming a common flow path in which anaesthetic liquid from the supply container and gas displaced from the anaesthetic liquid container are intermixed during filling of the anaesthetic liquid container, said intermediate container defining a liquid flow outlet level and a gas flow outlet level such that anaesthetic liquid is allowed to flow into the anaesthetic liquid container from the supply container to fill the anaesthetic liquid container to the desired level only when the liquid flow outlet level is below the gas flow outlet level, movement of the intermediate container with respect to normal operative orientation of the anaesthetic liquid container when the anaesthetic liquid container is tilted serving to stop the filling of the anaesthetic liquid container by causing the liquid flow outlet level to rise above the gas flow outlet level.

2. An arrangement according to claim 1 wherein said bent tubular member lies in a plane that is generally parallel to the horizontal reference plane when the anaesthetic liquid container is in the normal operative orientation, and wherein said bent tubular member is bent by at least 90°.

3. An arrangement according to claim 1 wherein, when the anaesthetic liquid container is in the normal operative orientation, said bent tubular member has, in a cross section taken normal to the horizontal reference plane, a bottom portion and an upper portion above said bottom portion, a highest point of said bottom portion defining said liquid flow outlet level and a lowest point of said upper portion defining said gas flow outlet level.

4. An arrangement according to claim 1 wherein said bent tubular member lies in a plane that is generally parallel to the horizontal reference plane when the anaesthetic liquid container is in the normal operative orientation, and wherein said bent tubular member is substantially U-shaped.

5. An arrangement according to claim 1 wherein said bent tubular member lies in a plane that is generally parallel to the horizontal reference plane when the anaesthetic liquid container is in the normal operative orientation and wherein said bent tubular member includes an S-shaped portion.

6. An arrangement according to claim 1 wherein said bent tubular member lies in a plane that is generally parallel to the horizontal reference plane when the anaesthetic liquid container is in the normal operative orientation, and wherein said bent tubular member is bent in a spiral.

7. An arrangement according to claim 1 wherein said bent tubular member is positioned within said anaesthetic liquid container.

8. An arrangement according to claim 7 wherein said intermediate container has said other end mounted to the filling port of the anaesthetic liquid container.

9. An arrangement according to claim 1 wherein said bent tubular member is positioned outside of said anaesthetic liquid container.

10. An arrangement according to claim 9 wherein said bent tubular member is positioned within said vaporizer.

11. An arrangement according to claim 1 wherein said bent tubular member is positioned outside said vaporizer.

12. An arrangement according to claim 11 wherein said bent tubular member is integral with said supply container.

13. An arrangement according to claim 11 wherein said bent tubular member comprises a separable element coupled to said supply container.

14. An arrangement according to claim 1 wherein said bent tubular member is formed from a single tube.

15. An arrangement according to claim 1 wherein said bent tubular member is formed of a plurality of tubes.

16. An arrangement according to claim 15 wherein said plurality of tubes lie in a common plane that is generally parallel to the horizontal reference plane when the anaesthetic liquid container is in the normal operative orientation.

17. An arrangement according to claim 15 wherein said plurality of tubes lie in different planes, each of said planes being generally parallel to the horizontal reference plane when the anaesthetic liquid container is in the normal operative orientation.

18. An arrangement according to claim 17 wherein said tubes lie in a plurality of common planes each of which is generally parallel to the horizontal reference plane when the anaesthetic liquid container is in the normal operative orientation, said common planes being spaced in a direction normal to the horizontal reference plane.

19. An arrangement according to claim 1 wherein said tubular member has, in a cross section taken normal to the horizontal reference plane, a diameter, and wherein said intermediate container has a portion projecting downward in a vertical direction when the anaesthetic liquid container is in the normal operative orientation by an amount greater than the diameter of said tubular member.

* * * * *